US007033320B2

(12) United States Patent
Von Behren et al.

(10) Patent No.: US 7,033,320 B2
(45) Date of Patent: Apr. 25, 2006

(54) EXTENDED VOLUME ULTRASOUND DATA ACQUISITION

(75) Inventors: Patrick L. Von Behren, Bellevue, WA (US); Jian-Feng Chen, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 246 days.

(21) Appl. No.: 10/635,193

(22) Filed: Aug. 5, 2003

(65) Prior Publication Data

US 2005/0033173 A1    Feb. 10, 2005

(51) Int. Cl.
A61B 8/00        (2006.01)
(52) U.S. Cl. ...................................... 600/443; 128/916
(58) Field of Classification Search ................ 600/437, 600/440, 443, 447, 453–456, 458; 128/916
See application file for complete search history.

(56) References Cited

U.S. PATENT DOCUMENTS

| | | | |
|---|---|---|---|
| 5,575,286 A | 11/1996 | Weng et al. | |
| 5,582,173 A | 12/1996 | Li | |
| 5,655,535 A | 8/1997 | Friemel et al. | |
| 5,782,766 A | 7/1998 | Weng et al. | |
| 5,876,342 A | 3/1999 | Chen et al. | |
| 5,899,861 A | 5/1999 | Friemel et al. | |
| 5,910,114 A | 6/1999 | Nock et al. | |
| 6,014,473 A | 1/2000 | Hossack et al. | |
| 6,059,727 A | 5/2000 | Fowlkes et al. | |
| 6,306,091 B1 * | 10/2001 | Sumanaweera et al. | 600/443 |
| 6,352,508 B1 | 3/2002 | Pang et al. | |
| 6,364,835 B1 | 4/2002 | Hossack et al. | |
| 6,500,118 B1 * | 12/2002 | Hashimoto | 600/437 |
| 6,572,549 B1 * | 6/2003 | Jong et al. | 600/443 |
| 6,582,367 B1 * | 6/2003 | Robinson et al. | 600/443 |
| 6,780,152 B1 * | 8/2004 | Ustuner et al. | 600/443 |
| 2003/0097068 A1 * | 5/2003 | Hossack et al. | 600/443 |

OTHER PUBLICATIONS

"Vein Graft Surveillance Using 3D Ultrasound Imaging Measurement of abdominal Aortic Aneurysm with 3D Ultrasound Tumor Measurement and Localization With 3D Imaging Automated Measurement of Flow-Mediated Vessel Dilation," by Daniel F. Leotta, Ph.D; Funded by the National Institutes of Health National Cancer Institute (2003 Research in the Department of Surgery).

"Three-Dimensional Spatial Compounding of Freehand Ultrasound Scans of the Rotator Cuff," by D. F. Leotta and R. W. Martin; hhtp://faculty.washington.edu/leotta/research/aium.html; dated Mar. 1999 (printed Jun. 27, 2003).

"Three-Dimensional Spatial Compounding of Ultrasound Scans with Incidence angle Weighting," by D. F. Leotta and R. W. Martin; 1999 IEEE International Ultrasonics Symposium; http//faculty.washington.edu/leotta/research/ieee99.html (printed Jun. 27, 2003.

"Three-Dimensional Ultrasound Imaging of the Rotator Cuff: Spatial Compounding and Tendon Thickness Measurement," by D. F. Leotta and R. W. Martin; http://faculty.washington.edu/leotta/research/shoulder_umb.html; Ultrasound Med. Bidiol. 26-509-525, 2000.

"Quantitative Three-Dimensional Echocardiography by Rapid Imaging from Multiple Transthoracic Windows: In Vitro Validation and initial in Vivo Studies," by D.F. Leotta B. Munt, EL Bolson, C. Kraft, R. W. Martin, C. M. Otto and F. H. Sheehan; National Library of Medicine; Am. Soc. Echocardiogr. (printed on Feb. 19, 2003).

"Sequential Freehand 3-D Ultrasound," Graham Treece's Ph.D. Research; Department of Engineering—University of Cambridge; http://svr-www.eng.cam.ac.uk/gmt11/research/volume.html (printed Jun. 16, 2003).

"3D Ultrasound Using Stradx 6.5," by R. Prager, A. Gee and Graham Treece; The Stradx 3D Ultrasound Acquisition and Visualization System; http://svr-www.eng.cam.ac.jk/rwp/stradx (printed on Jun. 16, 2003).

"Regularized Marching Tetrahedra: Improved Iso-Surface Extraction," by G. M. Treece, R.W. Prager and A. H. Gee; Cambridge University University Engineering Department, England, dated Sep. 1998.

Surface Interpolation From Sparse Cross-Sections Using Region Correspondence,: by G. M. Treece, R. W. Prager, A. H. Gee, and L. Berman; Cambridge University Engineering Department, England; dated Mar. 1999.

* cited by examiner

Primary Examiner—Francis J. Jaworski

(57) ABSTRACT

Three or four-dimensional ultrasound data acquisition for extended field of view imaging is provided. Multiple volumes are registered with respect to each other and spliced together to form an extended volume. The extended volume is a contiguous volume larger than a volumetric region that a multi-dimensional or wobbler transducer array is capable of imaging without movement. Information representing different volumes is registered with respect to each other by sensing the transducer position associated with each of the different volumes. The position is sensed using a position sensing mechanism, such as magnetic optical or gyroscope measurements. Acoustic data may be used to determine decorrelation of speckle or correlation of features to sense position. After the volumes are registered, any overlapping regions are compounded. The resulting extended field of view volume is displayed and manipulated for viewing by the user. A large volume or extended volume of the patient is used for assessing an organ, such as an entire fetus in OB applications.

22 Claims, 1 Drawing Sheet

US 7,033,320 B2

EXTENDED VOLUME ULTRASOUND DATA ACQUISITION

BACKGROUND

This present invention relates to three-dimensional imaging. In particular, three-dimensional ultrasound imaging of a large or elongated region of a patient is provided.

Commercially available ultrasound systems perform three-dimensional (3D) and four-dimensional (4D) volumetric imaging. Using a volumetric imaging transducer, such as a multidimensional array or a wobbler transducer, ultrasound energy is transmitted and received along scan lines within a volume region or a region that is more than a two-dimensional plane within the patient. For some applications, the transducer geometry limits scanning to only a portion of the desired volume. For extended objects such as the liver or a fetus, the transducer scans only a section of the anatomical feature.

Other 3D and 4D ultrasound systems use one-dimensional transducers to scan in a given plane. The transducer is translated or moved to various positions, resulting in a stack of planes with different relative spatial relationships representing a volume region of the patient. However, the relative position information and associated alignment of data may be inaccurate as compared to scans using multi-dimensional or wobbler transducers.

BRIEF SUMMARY

The present invention is defined by the following claims, and nothing in this section should be taken as a limitation on those claims. By way of introduction, the preferred embodiments described below include methods and systems for three-dimensional ultrasound data acquisition for extended field of view three-dimensional imaging. Multiple volumes are registered with respect to each other and spliced together to form an extended volume. Information representing individual volumes, possibly partially overlapping, is registered with respect to each other by sensing the transducer position associated with each of the individual volumes. The position is sensed using a position sensing mechanism, such as magnetic optical or gyroscope measurements. Acoustic data may be used to determine decorrelation of speckle or correlation of features between volumes to sense position. After the volumes are registered, any overlapping voxels may be compounded. The resulting extended field of view volume is displayed and manipulated for viewing by the user. The extended volume is a contiguous volume larger than a volumetric region that a multi-dimensional or wobbler transducer array is capable of imaging without displacement. A large volume or extended volume of the patient is used for assessing an organ, such as an entire fetus in OB applications, or in surgical planning.

In a first aspect, a method for three-dimensional ultrasound data acquisition is provided. First and second sets of ultrasound data representing first and second three-dimensional volumes respectively of a patient are acquired with a volumetric imaging transducer. The first three-dimensional volume overlaps with but is different than the second three-dimensional volume. Ultrasound data from the first set is combined with ultrasound data from the second set.

In a second aspect, a three-dimensional ultrasound data acquisition system is provided for extended field of view three-dimensional imaging. The system includes a volumetric imaging transducer for acquiring the sets of data discussed above and a processor operable to combine the ultrasound data as discussed above.

In a third aspect, a method for three-dimensional ultrasound data acquisition is provided. A transducer probe is translated between two different positions relative to a patient. Acoustic energy is steered from the transducer probe at two or more different angles relative to the transducer probe during the translation. The two different angles are along a dimension substantially parallel to a direction of the translation of the transducer probe. Ultrasound data responsive to the translation and steering is stored. The ultrasound data represents different three-dimensional regions of the patients at the different positions. A relative spacing of the two different positions is determined. The ultrasound data is combined as a function of the relative spacing.

Further aspects and advantages of the invention are discussed below in conjunction with the preferred embodiments.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
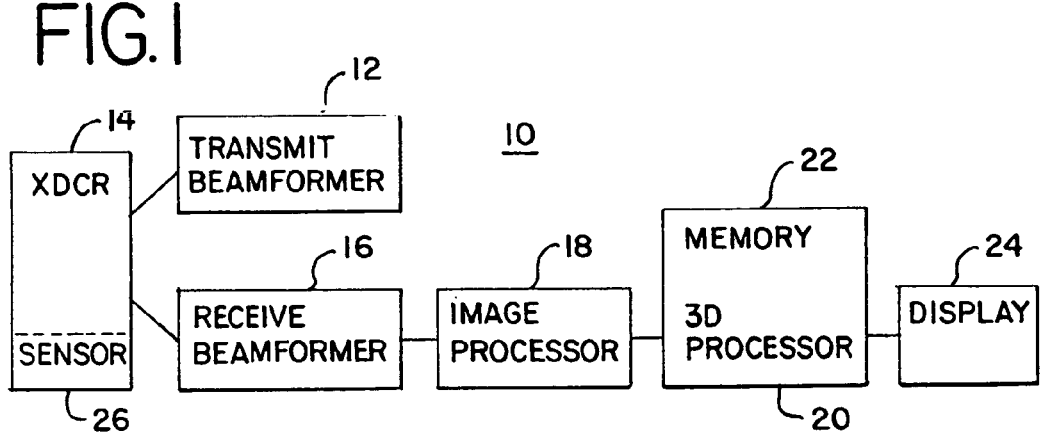
FIG. 1 is a block diagram of one embodiment of an ultrasound system for three-dimensional imaging.

FIG. 1 shows a block diagram of a medical diagnostic ultrasonic imaging system 10 for three- or four-dimensional imaging. Three-dimensional imaging provides representations of a volume region as opposed to a planar region of a patient at a given time. Four-dimensional imaging provides a representation of a three-dimensional volume as a function of time, such as to show motion of features within the volume. The system 10 comprises any of now known or later developed ultrasound systems for three-dimensional imaging.

A transmit beamformer 12 includes memories, delays, amplifiers, waveform generators, oscillators, filters, modulators, analog devices, digital devices and combinations thereof for generating a plurality of waveforms in various channels. The waveforms are apodized and delayed relative to each other for electronic steering in either one or two dimensions, such as steering within a plane or steering within a volume or plurality of planes, respectively. Either full or sparse sampling may be provided, resulting in greater or fewer numbers of waveforms to generate for any given scan line. The transmit beamformer 12 applies the transmit waveforms to a volumetric imaging transducer 14.

The volumetric imaging transducer 14 is a multi-dimensional array, such as a two-dimensional array or other array of N by M elements where both N and M are greater than 1. By having a multi-dimensional array of elements, the volumetric imaging transducer 14 is operable to scan with scan lines electronically steerable in two dimensions, such as scanning a volume for voxels extending along any of three dimensions. As a result of scanning along scan lines in two dimensions, multiple voxels are provided along any given azimuth, elevation and range dimension, resulting in a volumetric representation or scan.

In another embodiment, the volumetric imaging transducer 14 is a wobbler transducer. Any now known or later developed linear, one-dimensional array or single element is provided. The wobbler is mechanically steered in one or two dimensions and electrically steered in no or one dimension. In one embodiment, the scan lines are mechanically steered in one dimension, such as along an elevation dimension and electronically steered due to delays and apodization of waveforms from the transmit beamformer 12 in another dimension, such as the azimuth dimension. A wobbler array with electric steering in two dimensions may also be provided.

Other now known or later developed volumetric imaging transducers operable to acquire ultrasound data representing a volume with a greater extent than a planar slice of the patient may be used.

The volumetric imaging transducer 14 is operable to acquire a set of ultrasound data representing a three-dimensional volume of a patient. By directing scan lines at different positions within two dimensions, and receiving as a function of time representing the depth dimension, a three-dimensional volume may be scanned with the transducer without movement of the transducer 14. Given the speed of sound through tissue, a volume is scanned even with movement of the transducer 14 by directing scan lines at different angles along the azimuth and elevation dimensions during translation. As a result, the volumetric imaging transducer 14 is used to acquire multiple sets of ultrasound data representing different three-dimensional volumes while stationary or while moving. The three-dimensional volumes overlap but represent different overall regions. In one embodiment, the overlap is just along the elevation dimension, but the transducer may be moved along more than one axis and/or rotated, resulting in overlap along any of three dimensions.

Optionally, the transducer 14 includes a position sensor, such as a dedicated sensor for determining a position of the transducer 14 within a volume, area or adjacent to the patient. The sensor 26 is any now known or later developed magnetic, optical, gyroscope or other physical position measurement device. For example, electromagnetic coils positioned in the sensor are used to determine the position and orientation of the transducer 14 within a room. In alternative embodiments, the transducer 14 is free of a position sensor 26.

A receive beamformer 16 receives electrical signals generated by the transducer 14. The receive beamformer 16 has one or more delays, amplifiers, filters, demodulators, analog components, digital components and combinations thereof separated into a plurality of channels with a summer for summing the information from each of the channels. The summer or a subsequent filter outputs in-phase in quadrature or radio frequency data. Any now known or later developed receive beamformers may be used. The receive beamformer 16 outputs ultrasound data representing one or more scan lines to an image processor 18.

The image processor 18 is a digital signal processor, control processor, general processor, application specific integrated circuit, analog circuitry, digital circuitry or combination thereof. The image processor 18 detects intensity or B-mode information, estimates flow or Doppler information, or detects any other characteristic of the ultrasound data. The image processor may also implement temporal, spatial or frequency filtering. In one embodiment, the image processor 18 includes a scan converter, but a scan converter may be provided after a 3D processor 20 or as part of the 3D processor 20. One or more memories or buffers, such as a CINE memory, are optionally provided in the image processor 18. The image processor 18 outputs the detected ultrasound data to the 3D processor 20 in a polar coordinate, Cartesian coordinate or other format. Alternatively, the ultrasound data is output directly to a memory 22.

The 3D processor 20 is a general processor, digital signal processor, application specific integrated circuit, computer, digital processor, analog processor, combinations thereof or other now known or later developed processor for generating a three-dimensional representation from data representing a volume region. In one embodiment, the 3D processor 20 is a processor used for or with other components of the system 10, such as a control processor for controlling the image processor 18. A separate or dedicated 3D processor 20 may be used.

The memory 22 is a RAM, buffer, portable, hard drive or other memory now known or later developed. In one embodiment, the memory 22 is part of another component of the system 10, such as CINE memory, a memory of the image processor 18 or a display plane memory, but a separate memory for three-dimensional processing may be provided.

The 3D processor 20 is operable to combine ultrasound data representing one volume with ultrasound data representing a different volume, such as combining a first set with a second set. The combination is performed as a function of the relative positions of the volumes. For example, the 3D processor 20 receives position information from the sensor 26 or determines relative position information from the ultrasound data. The data of one set is positionally related to the data of another set based on the relative positions of the transducer 14 when the data was acquired. The data representing one volume is combined with the data representing another volume to form an extended volume. Alternatively, a subset of one, both or multiple of sets of ultrasound data representing different volumes are combined.

Ultrasound data used for determining position is all of or subsets of one or more of the volumes being combined. For example, data representing a likely overlapped area, such as associated with data adjacent to an edge of the volume in the direction of translation of a transducer 14 of one volume is compared with data likely overlapping. In alternative embodiments, data from one of the sets of volume data is compared to data not used for three-dimensional imaging to determine the translation and associated positions of the transducer 14. Any combinations of data not used for three-dimensional imaging, data used for the three-dimensional imaging and combinations thereof may be used.

The 3D processor 20 uses the combined data to generate a three-dimensional representation. The combined data is formatted in a polar coordinate, Cartesian or 3D grid. The data is interpolated or otherwise selected for rendering. Any of surface, volume or other now known or later developed techniques for generating an image representing a three-dimensional volume may be used.

The display 24 is a CRT, monitor, plasma screen, LCD, projector or other display device for generating an image representing the 3D volume. Using the 3D processor 20 and the display 24, the user may cause the image to be rotated or dissected for viewing the information within the three-dimensional volume from different angles or perspectives.

In one embodiment, the 3D processor 20 and the display 24 are a separate workstation from the rest of the system 10, such as a workstation within the system 10 or remote from the system 10.

Figure 2:
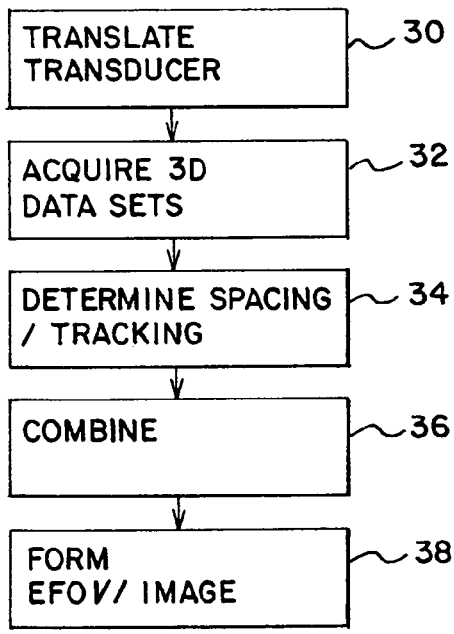
FIG. 2 is a flow chart representing one embodiment of extended field of view three-dimensional imaging.

FIG. 2 shows a flow chart of a method for three-dimensional ultrasound acquisition. Additional, different or fewer acts may be provided. The method of FIG. 2 is implemented using the system 10 of FIG. 1 or a different system.

In act 30, the transducer probe housing the transducer 14 is translated or moved between two different positions relative to the patient. In one embodiment, the transducer probe is slowly moved while different sets of data representing volumes are acquired. For example, the transducer is moved at about an inch per second so that ultrasound signals for 128 lines in 100 different slices are acquired for a given volume. Due to the speed of sound, the volume is acquired at a substantially same position of the transducer 14 even given the continuous movement of the transducer probe. Accordingly, multiple volumes are acquired at different transducer positions without ceasing movement of the transducer probe. Thirty or another number of volumes may be acquired each second, such as acquiring about 23 volumes a second for three seconds (total of about 70 volumes to be combined). More rapid or slower translation and associated scanning of a greater or lesser volume may be used. A sound or graphic may be provided to the user for indicating a desired translation speed. In alternative embodiments, the transducer probe is moved from one position to a second position and maintained at each of the positions for a time period, such as associated with acquiring ultrasound data for two different volumes through two different discrete acoustic windows.

In act 32, a plurality of ultrasound data sets representing a three-dimensional volume are acquired. For example, the data sets are acquired with the volumetric imaging transducer 14 while being translated over the patient. As shown in FIG. 3A, two volumes 40 and 42 are acquired associated with translating the transducer 14 from or through a position 44 to or past the position 46. As a result, the ultrasound data representing the volume 40 overlaps with the ultrasound data representing the volume 42. While the transducer positions 44 and 46 do not overlap, some overlap may be provided or the positions may be further separated.

Acoustic energy is steered from the transducer 14 at two or more different angles relative to the transducer 14 to scan each volume 40, 42. As shown by the scan lines 48 and 50, two of the different angles used are along a dimension substantially parallel to the direction of translation. Any number of scan lines and associated angles may be used. As a result of the different angles along the direction of translation as well as along another dimension, data representing a volume is acquired.

As discussed above, the ultrasound data representing the first volume 40 is acquired with the transducer 14 held at a stationary position 44 or as the transducer 14 is translated without stopping through the position 44. Likewise, the ultrasound data representing the second volume 42 is acquired with the transducer held in the position 46 or as the transducer 14 is translated through the position 46. Where the transducer 14 is held substantially stationary, substantially is provided to account for movement due to breathing, heart motion or unintentional movement of the sonographer or patient. Where the volumes 40, 42 are acquired while translating the transducer 14 without stopping at each position, the sets of data are acquired sufficiently rapidly in comparison to the rate of translation of the transducer to allow acquisition of the volume. Where the translation of the transducer 14 causes a perceived compression of the data, interpolation, morphing or other techniques may be used to account for motion of the transducer 14 in acquisition of data throughout the volume.

Figure 3:
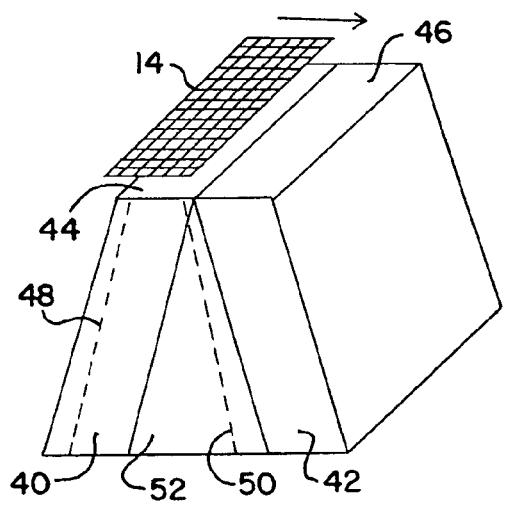
FIG. 3 is a graphical representation showing one embodiment of acquiring two volumes while translating a transducer.

As shown in FIG. 3, a portion of ultrasound data representing each of the volumes 40 and 42 is an overlapping region 52. Data from each of the volumes 40 and 42 represent the overlapping region 52. The data may or may not occur at the identical spatial location within the overlapping region 52.

While only two volumes 40 and 42 are shown, additional volumes with more or less overlap may be provided, including an initial volume and an ending volume with no overlap. The overlap shown in FIG. 3 is associated with transducer positions 44 and 46 along one dimension, such as the elevation dimension. Rotation and translation along other or additional dimensions relative to the transducer 14 array may be provided.

The acquired ultrasound data is left in a same polar coordinate or Cartesian coordinate format. Alternatively, the data representing the volumes is reformatted onto a 3D grid that is common for all volumes. The ultrasound data representing the various three-dimensional volumes of the patient is stored. In one embodiment, each of the sets of data representing a different volume is stored separately. In alternative embodiments, the ultrasound data is combined and then stored after combination.

In act 34, a relative spacing of the first position 44 to the second position 46 is determined. The positioning is determined within the three dimensional space accounting for translation and rotation. Alternatively, positions along a single dimension without rotation or other dimensional translation is determined.

In one embodiment, the position of the volumetric imaging transducer 14 is tracked using ultrasound data. The relative spacing between the two positions is determined from the ultrasound data. The ultrasound data used for the tracking is the data from one, both, or different data than the sets of data representing the three-dimensional volumes. Filtering, correlation, the sum of absolute differences, decorrelation or other techniques are used for identifying and registering speckle or features from one data set in a different data set. For example, speckle or features are isolated and used to determine a pattern from one set of data that is most similar to a pattern of another set of data. The amount of translation and rotation of the best pattern match provides a vector representing translation and identifies a rotation. In one embodiment, a pattern based on a subset of the ultrasound data of one volume is used for matching with another set. Alternatively, multiple subsets of data representing spatially different volumes or planes along different dimensions are used for the pattern matching. Alternatively, all of the data of one data set is pattern matched with all of the data of another data set. As yet another alternative, sub-sampling of the entire data set or portions of a data set are used to match against a sub-sampling or full sampling of another data set.

Any of various now known or later developed two-or three-dimensional techniques for determining positions from the data may be used, such as disclosed in U.S. Pat. Nos. 5,876,342, 5,575,286, 5,582,173, 5,782,766, 5,910, 114, 5,655,535, 5,899,861, 6,059,727 and 6,014,473, the disclosures of which are incorporated herein by reference. Any of the two-dimensional correlation, decorrelation, or motion tracking techniques discussed in the patents above or now known or later developed may be used or expanded for correlation and tracking of speckle or features in a three-dimensional volume or using a three-dimensional data set for the correlations or other calculations. For speckle tracking, decorrelation or correlation is determined. For feature tracking, a sum of absolute differences is determined. In one embodiment, both speckle and feature information are tracked and the combined translation and rotation information, such as an average, is used. Since additional speckle and structural information is provided in a three-dimensional volume as opposed to a planar image, the registration of one volume relative to another volume may be more accurate and accomplish more degrees of freedom rather than relying on an elevation speckle decorrelation in a two-dimensional image. The determined translation and rotation or registration information provides the relative positions between various transducer positions 44 and 46 for acquiring ultrasound data representing the different volumes. The position information also provides a relationship information for various voxels within the overlapping region 52.

In an alternative embodiment, the relationship between the different positions 44 and 46 of the volumetric imaging transducer 14 is provided by a sensor 26 on the transducer 14. The sensor 26 mounted on the transducer 14 provides an absolute position within a room or volume or provides a difference in position from a previous position, such as providing an amount of motion and direction as a function of time. In either case, the difference in translation and/or rotation between two different transducer positions 44, 46 and the associated spatial relationship of the ultrasound data representing the volumes 40 and 42 is determined.

Figure 4:
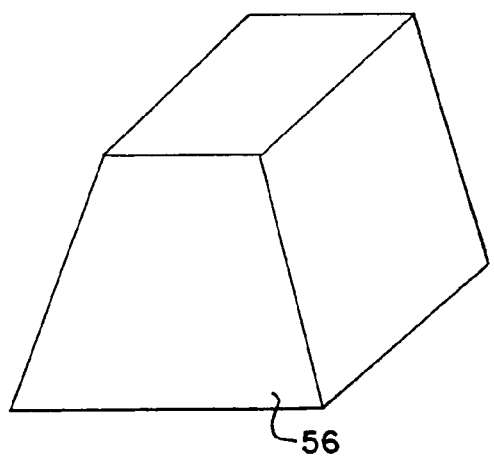
FIG. 4 is a graphical representation of an extended field of view volume in one embodiment.

In act 36, different sets of ultrasound data representing the different volumes are combined. Each set of ultrasound data is aligned relative to other sets of data as a function of the determined spacing of act 34 for combination. The two volumes 40 and 42 shown in FIG. 3 are aligned as shown and combined to form the volume 56 shown in FIG. 4. In the overlapping region 52, the ultrasound data from the first set is compounded with the ultrasound data from the second set, such as averaging or weighted averaging. Any of various combination techniques may be used, such as selecting a maximum or minimum value, or adaptively compounding as a function of amount of correlation, type of data, signal-to-noise ratio of data or other parameters determined from the ultrasound data or the sensor 26. In one embodiment, a finite impulse response filtering with an equal weighted averaging of one or more values associated with a particular location on a 3D grid from any or all sets of data overlapping at that location is performed. For example, the nearest four pixel values to a 3D grid point for each set of data are weighted as a function of the distance of the data value from the grid point with equal or spatially related weighting being applied between the sets of data. The resulting compounded values are normalized. Any of various now known or later developed interpolation and compounding techniques may be used. In alternative embodiments, interpolation to the 3D grid and combination of ultrasound data from different data sets is performed separately.

Regions where only one set of data represents the region are included in the combination without averaging or other alteration. Alternatively, these regions are either removed or the ultrasound data is increased or decreased to account for processing of the overlapped regions to avoid stripes or differences in gain. In one embodiment avoiding compounding in the combination, ultrasound data from only non-overlapping regions are added to the ultrasound data set of another volume, such as growing the combined volume without compounding data points from different sets presenting a same or substantially same spatial location.

In one embodiment, the ultrasound data representing a feature or a volume in general is morphed or altered as a function of pressure distortion prior to combination. In alternative embodiments, the morphing occurs after combination. For example, the ultrasound data is interpolated to account for pressure, such as caused by the transducer compressing or warping an organ while being placed on the skin or caused by heart cycle pressure placed on the organ.

In act 38, a three-dimensional representation image responsive to the combined ultrasound data is formed or generated. For example, a maximum intensity projection, minimum intensity projection or weighted intensity projection is volume rendered for one or a plurality of different look directions relative to the volume 56. Alternatively, a surface rendering with or without associated shading is generated as an image. Any of various now known or later developed three-dimensional imaging techniques given ultrasound data representing the volume may be used.

The displayed three-dimensional representation provides an extended field of view. Rather than providing a three-dimensional image based on each of the volumes 40 and 42 separately, a three-dimensional image representing the combined volume 56 is provided. This extended field of view in three dimensions is larger than a region or view acquired with the transducer 14 held stationary. In one embodiment, the ultrasound data for the entire combined region 56 is used to generate the three-dimensional representation. Alternatively, ultrasound data of selected portions of the combined region 56 is used, such as only using a first portion of either the first volume 40 or second volume 42. For the extended field of view, at least a portion of one of the data sets is included for generating a three-dimensional representation with data from the other data set.

While described above for two volumes generally, three or more volumes may be combined as discussed herein. Multiple volumes are spliced together to visualize larger organs as one composite volume and may provide different levels of compounding. The composite volume may be reacquired multiple times to provide an extended field of view 4D imaging (i.e. 3D imaging with the composite volume as a function of time).

A composite volume three-dimensional representation may be displayed while acquiring multiple three-dimensional representations. Other displays representing either a component volume or the combined volume, such as an arbitrary slice through the volumes, may be generated before a final display. Other two-dimensional images may be displayed while acquiring the component volume sets of data or while displaying the compounded or composite three-dimensional representation. The extended field of view three-dimensional representation is used for 3D surgical planning. Four-dimensional functional or panoramic images information may be detected and displayed, such as imaging with strain information or contrast agent perfusion, inflow or outflow information within or as the compound volume three-dimensional representation. B-mode, Doppler or other types of information are used independently or together for the display of the three-dimensional representation. For example, a power mode Doppler display is generated without B-mode information from Doppler data acquired for multiple volumes.

While the invention has been described above by reference to various embodiments, it should be understood that many changes and modifications can be made without departing from the scope of the invention. For example, for real time tracking with minimal processing, the user is instructed to translate along one dimension and the motion is tracked just along one dimension, such as the elevation dimension. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional ultrasound data acquisition, the method comprising:
   (a) acquiring first and second sets of ultrasound data representing first and second three-dimensional volumes, respectively, of a patient with a volumetric imaging transducer, the first three-dimensional volume overlapping with but different than the second three-dimensional volume, the first and second three-dimensional volumes having x, y and z dimensions, each of x, y and z extending for multiple voxels; and
   (b) compounding ultrasound data from the first set with ultrasound data from the second set.

2. The method of claim 1 further comprising:
   (c) generating a three-dimensional representation image responsive to the combined ultrasound data.

3. The method of claim 2 wherein (c) comprises forming an extended field of view wherein the tree-dimensional representation image represents both of the first and second three-dimensional volumes including at least a first portion of the first three-dimensional volume outside the second three-dimensional volume and at least a second portion of the second three-dimensional volume outside the first three-dimensional volume.

4. The method of claim 1 wherein the volumetric imaging transducer comprises a transducer, wherein (a) comprises acquiring the first and second sets of data while translating the transducer.

5. The method of claim 1 wherein (a) comprises acquiring with the volumetric imaging transducer being one of a wobbler transducer and a multi-dimensional transducer array operable to scan the first and second three dimensional volumes.

6. The method of claim 1 wherein (b) comprises:
   (b1) aligning the first set of data relative to the second set and data; and
   (b2) compounding the aligned first and second sets of data.

7. The method of claim 1 further comprising:
   (c) tracking a position of the volumetric imaging transducer during (a).

8. The method of claim 7 wherein (c) comprises tracking the position with a device mounted on the volumetric imaging transducer.

9. The method of claim 7 wherein (c) comprises determining the position from ultrasound data consisting of: the first set, the second set, both the first and second sets, data different than the first and second sets and combinations thereof.

10. The method of claim 9 wherein (c) comprises determining the position using one of feature and speckle tracking.

11. The method of claim 1 wherein acquiring comprises acquiring with the first and second three-dimensional volumes each being a region that is more than a two-dimensional plane within the patient.

12. The method of claim 1 wherein the overlapping is overlapping by multiple scan planes.

13. A method for three-dimensional ultrasound data acquisition, the method comprising:
   (a) acquiring first and second sets of ultrasound data representing first and second three-dimensional volumes, respectively, of a patient with a volumetric imaging transducer, the first three-dimensional volume overlapping with but different than the second three-dimensional volume, the first and second three-dimensional volumes having x, y and z dimensions, each of x, y and z extending for multiple voxels; and
   (b) combining ultrasound data from the first set with ultrasound data from the second set;
   wherein the volumetric imaging transducer comprises a transducer, wherein (a) comprises acquiring the first set of data with the transducer at a substantially stationary first position and acquiring the second set of data with the transducer at a substantially stationary second position different than the first position.

14. A method for three-dimensional ultrasound data acquisition, the method comprising:
   (a) acquiring first and second sets of ultrasound data representing first and second three-dimensional volumes, respectively, of a patient with a volumetric imaging transducer, the first three-dimensional volume overlapping with but different than the second three-dimensional volume, the first and second three-dimensional volumes having x, y and z dimensions, each of x, y and z extending for multiple voxels;
   (b) combining ultrasound data from the first set with ultrasound data from the second set; and
   (c) morphing a feature of the first set of ultrasound data as a function of pressure distortion.

15. A three-dimensional ultrasound data acquisition system for extended field of view three-dimensional imaging, the system comprising:
   a volumetric imaging transducer operable to acquire first and second sets of ultrasound data representing first and second three-dimensional volumes, respectively, of a patient, the first three-dimensional volume overlapping with but different than the second three-dimensional volume, the first and second three-dimensional volumes having x, y and z dimensions, each of x, y and z extending for multiple voxels; and
   a processor operable to compound ultrasound data from the first set with ultrasound data from the second set.

16. The system of claim 15 wherein the volumetric imaging transducer comprises a multi-dimensional array operable to scan with scan lines steerable in two dimensions.

17. The system of claim 15 wherein the volumetric imaging transducer comprises a wobbler transducer operable to scan with scan lines steerable in two dimensions.

18. The system of claim 15 further comprising an electromagnetic position sensor connected with the volumetric imaging transducer.

19. The system of claim 15 wherein the processor is operable to determine positions of the volumetric imaging transducer relative to the patient from ultrasound data consisting of: the first set, the second set, both the first and second sets, data different than the first and second sets and combinations thereof.

20. A method for three-dimensional ultrasound data acquisition, the method comprising:
   (a) translating a transducer probe between first and second positions relative to a patient, the first position different than the second position;
   (b) steering acoustic energy from the transducer probe at two or more different angles relative to the transducer probe during (a), the two different angles being along a dimension substantially parallel to a direction of the translation of (a);

(c) storing ultrasound data responsive to (a) and (b) and representing first and second three-dimensional regions of the patient at the first and second positions, respectively, the first and second three-dimensional regions having x, y and z dimensions, each of x, y and z extending for multiple voxels;

(d) determining a relative spacing of the first position to the second position; and (e) compounding the ultrasound data representing the first three-dimensional region with the ultrasound data representing the second three-dimensional region as a function of the relative spacing.

21. The method of claim 20 further comprising:

(f) displaying a three-dimensional representation of an extended field of view of the combined first and second three-dimensional regions, the combined first and second three-dimensional regions being larger than the transducer probe is operable to acquire without translation.

22. The method of claim 20 wherein (d) comprises determining the relative spacing from ultrasound data.

* * * * *